(12) United States Patent
Wipf et al.

(10) Patent No.: US 6,803,475 B2
(45) Date of Patent: Oct. 12, 2004

(54) FLUOROUS TAGGING COMPOUNDS AND METHODS OF USE THEREOF

(75) Inventors: Peter Wipf, Pittsburgh, PA (US); Stephan Roever, Inzlingen (DE)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 10/690,935

(22) Filed: Oct. 22, 2003

(65) Prior Publication Data

US 2004/0082792 A1 Apr. 29, 2004

Related U.S. Application Data

(62) Division of application No. 09/583,247, filed on May 31, 2000, now Pat. No. 6,673,539.

(51) Int. Cl.[7] .............................. C07F 7/18; C07F 7/08
(52) U.S. Cl. ........................ 556/465; 556/413; 556/488; 556/489
(58) Field of Search ................................ 556/413, 465, 556/488, 489

(56) References Cited

U.S. PATENT DOCUMENTS

| | | |
|---|---|---|
| 4,454,233 A | 6/1984 | Wang |
| 5,401,847 A | 3/1995 | Glazer |
| 5,463,082 A | 10/1995 | Horvath |
| 5,777,121 A | 7/1998 | Curran |
| 5,798,032 A | 8/1998 | Khan |
| 5,859,247 A | 1/1999 | Curran |
| 6,156,896 A | 12/2000 | Curran |

OTHER PUBLICATIONS

Curran, D. P.; Luo, Z. Y. Fluorous synthesis with fewer fluorines (light fluorous synthesis): Separation of tagged from untagged products by solid–phase extraction with fluorous reverse–phase silica gel. J. Am. Chem. Soc. 1999, 121, 9069–9072.

Curran, D. P.; Hadida,S.; He, M. Thermal allylations of aldehydes with a fluorous allylstannane. Separation of organic and fluorous products by solid phase extraction with fluorous reverse phase silica gel. J. Org. Chem. 1997, 62, 6714–6715.

Curran, D. P. Strategy–level separations in organic synthesis: From planning to practice. Angew. Chem., Int. Ed. Eng. 1998, 37, 1175–1196.

Curran, D. P.; Ferritto, R.; Hua, Y. Preparation of a fluorous benzyl protecting group and its use in a fluorous synthesis approach to a disaccharide. Tetrahedron Lett. 1998, 39, 4937–4940.

Danielson, N. D.; Beaver, L. G.; Wangsa, J. Fluoropolymers and fluorocarbon bonded phases as column packings for liquid chromatography. J. Chromat. 1991, 544, 187–199.

Kainz, S.; Luo, Z. Y.; Curran, D. P.; Leitner, W. Synthesis of perfluoroalkyl–substituted aryl bromides and their purification over fluorous reverse phase silica. Synthesis 1998, 4125–1427.

Studer, A.; Hadida, S.; Ferritto, R.; Kim, S. Y.; Jeger, P. et al. Fluorous synthesis: A fluorous–phase strategy for improving separation efficiency in organic synthesis. Science 1997, 275, 823–826.

(List continued on next page.)

*Primary Examiner*—Rita Desai
*Assistant Examiner*—Raymond Covington
(74) *Attorney, Agent, or Firm*—Bartony & Hare, LLP

(57) ABSTRACT

A method of increasing the fluorous nature of a compound includes the step of reacting the compound with at least one second compound having the formula:

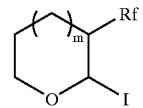

wherein Rf is a fluorous group and m is 0, 1 or 2.

9 Claims, 9 Drawing Sheets

OTHER PUBLICATIONS

Studer, A.; Curran, D. P. A strategic alternative to solid phase synthesis: Preparation of a small isoxazoline library by "fluorous synthesis". Tetrahedron 1997, 53, 6681–6696.

Studer, A.; Jeger, P.; Wipf, P.; Curran, D. P. Fluorous synthesis: Fluorous protocols for the ugi and biginelli multicomponent condensations. J. Org. Chem. 1997, 62, 2917–2924.

Wipf, P.; Reeves, J. T. Synthesis and applications of a fluorous thp protective group. Tetrahedron Lett. 1999, 40, 4649–4652.

Rover, S.; Wipf, P. Synthesis and applications of fluorous silyl protecting groups with improved acid stability. Tetrahedron Lett. 1999, 40, 5667–5670.

Wipf, P.; Reeves, J. T. Synthesis and applications of a highly fluorous alkoxy ethyl ether protective group. Tetrahedron Lett. 1999, 40, 5139–5142.

Wipf, P; Development of a Fluorous Strategy for Organic Synthesis, copy of four slides from oral presentation (Jan. 11, 1999).

Structural Variation of the Antimitotic Natural Product Curacin A: C(1)-C(18) Segment

US 6,803,475 B2

FLUOROUS TAGGING COMPOUNDS AND METHODS OF USE THEREOF

CROSS REFERENCE TO RELATED APPLICATIONS

This application is divisional patent application of U.S. patent application Ser. No. 09/583,247, filed May 31, 2000, the disclosure of which is incorporated herein by reference.

GOVERNMENTAL INTERESTS

This invention was made with government support under grant CA 78039 awarded by the National Institutes of Health. The government has certain rights in this invention.

FIELD OF THE INVENTION

The present invention relates to fluorous tagging or protecting compounds and to methods of use thereof, and especially, to fluorous tagging compounds suitable for use with hydyroxy- and amine-bearing organic compounds.

BACKGROUND OF THE INVENTION

In traditional organic chemistry, compounds are synthesized as pure substances through well-planned reactions and careful separation. However, in a number of fields, including drug discovery, catalyst design and new material development, tens of thousands of organic compounds must be synthesized and tested to discover a few active ones. In the pharmaceutical industry, for example, synthesizing such a large number of compounds in the traditional way is too slow compared to the rapid emergence of new biological targets. The productivity of orthodox solution (liquid) phase organic synthesis is severely limited by tedious separation processes for the purification of products. Techniques integrating organic reactions with rapid purification/separation procedures are thus highly desirable.

Recently, fluorous synthetic and separation techniques have attracted the interest of organic chemists. In fluorous synthetic techniques, reaction components are typically attached to fluorous groups or tags such as perfluoroalkyl groups to facilitate the separation of products. Organic compounds are readily rendered fluorous by attachment of an appropriately fluorinated phase label or tag. In general, fluorous-tagged molecules partition preferentially into a fluorous phase while non-tagged ones partition into an organic phase.

The fluorous tag preferably fulfills a double role as protective group and phase tag and is removed in the final step(s) of the synthesis. The viability of a fluorous synthesis plan depends greatly on the availability of suitable fluorous protecting groups, but only a few fluorous tags are currently available.

In that regard, the fluorous phase label or tag most often used in fluorous synthesis has been the silane $(C_{10}F_{21}CH_2CH_2)_3SiBr$ 1. In general, the silane is attached to alcohol-bearing substrates using standard conditions to result in a silyl ether, and can be cleaved with fluoride. The silane, however, cannot be recycled. In addition, the powerful electron withdrawing effect of three fluorous chains makes the silyl ether rather labile towards nucleophiles and other polar reactions. Thus, although fluorous synthetic and/or separation techniques are promising, such techniques are currently limited by a lack of availability of suitably versatile fluorous tags.

It is thus very desirable to develop improved fluorous tagging compounds.

SUMMARY OF THE INVENTION

For the further development of fluorous phase chemistry into a practical strategy in, for example, combinatorial and parallel synthesis, a variety of fluorous phase labels must be made available. The present invention provides fluorous tags that can be prepared in large quantity, can be installed and removed from a substrate using mild reaction conditions, and can be recyclable after cleavage. In addition, the fluorous tags of the present invention are tolerant, as a group, to a wide range of reaction conditions, such that an appropriate label can be chosen which is amenable to substantially any given sequence of reactions.

The resulting fluorous "tagged" compound can be used in a wide variety of fluorous reaction and/or separation techniques. Several fluorous reaction and separation techniques are disclosed, for example, in U.S. Pat. Nos. 5,859,247 and 5,777,121, the disclosures of which are incorporated herein by reference. The tagging compounds of the present invention are particularly suitable for tagging of compounds bearing hydroxyl groups or nitrogen groups such as amine groups.

As used herein, the term "fluorous", when used in connection with an organic (carbon-containing) molecule, moiety or group, refers generally to an organic molecule, moiety or group having a domain or a portion thereof rich in carbon-fluorine bonds (for example, fluorocarbons or perfluorocarbons, fluorohydrocarbons, fluorinated ethers, fluorinated amines and fluorinated adamantyl groups). For example, perfluorinated ether groups can have the general formula —[(CF$_2$)$_x$O(CF$_2$)$_y$]$_z$CF$_3$, wherein x, y and z are integers. Perfluorinated amine groups can, for example, have the general formula —[(CF$_2$)$_x$(NR$^a$)CF$_2$)$_y$]$_z$CF$_3$, wherein R$^a$ can, for example, be (CF$_2$)$_n$CF$_3$, wherein n is an integer. Fluorous ether groups and fluorous amine groups suitable for use in the present invention need not be perfluorinated, however. The term "fluorous compound," thus refers generally to a compound comprising a portion rich in carbon-fluorine bonds. As used herein, the term "perfluorocarbons" refers generally to organic compounds in which all hydrogen atoms bonded to carbon atoms have been replaced by fluorine atoms. The terms "fluorohydrocarbons" and "hydrofluorocarbons" include organic compounds in which at least one hydrogen atom bonded to a carbon atom has been replaced by a fluorine atom. A few examples of suitable fluorous groups Rf for use in the present invention include, but are not limited to, —C$_4$F$_9$, —C$_6$F$_{13}$, —C$_8$F$_{17}$, —C$_{10}$F$_{21}$, —C(CF$_3$)$_2$C$_3$F$_7$, —C$_4$F$_8$CF(CF$_3$)$_2$, —CF$_2$CF$_2$OCF$_2$CF$_2$OCF$_3$, —CF$_2$CF$_2$(NCF$_2$CF$_3$)CF$_2$CF$_2$CF$_3$, and fluorous adamantyl groups.

As used herein, the term "tagging" refers generally to attaching a fluorous moiety or group (referred to as a "fluorous tagging moiety" or "tagging group") to a compound to create a "fluorous tagged compound". Separation of the tagged compounds of the present invention is achieved by using fluorous separation techniques that are based upon differences between/among the fluorous nature of a mixture of compounds. As used herein, the term "fluorous separation technique" refers generally to a method that is used to separate mixtures containing fluorous molecules or organic molecules bearing fluorous domains or tags from each other and/or from non-fluorous compounds based predominantly on differences in the fluorous nature of molecules (for example, size and/or structure of a fluorous molecule or domain or the absence thereof). Fluorous separation techniques include but are not limited chromatography over solid fluorous phases such as fluorocarbon bonded phases or fluorinated polymers. See, for example, Danielson, N. D. et al., "Fluoropolymers and Fluorocarbon Bonded Phases as Column Packings for Liquid Chromatography," *J. Chromat.*, 544, 187–199 (1991). Examples of suitable fluorocarbon bonded phases include commercial Fluofix® and Fluophase™ columns available from Keystone Scientific, Inc. (Bellefonte, Pa.), and FluoroSep™-Octyl from ES Industries (Berlin, N.J.). Other fluorous separation techniques include liquid-liquid based separation methods such as liquid-liquid extraction or countercurrent distribution with a fluorous solvent and an organic solvent.

Preferably, the molecular weight of the fluorous tags of the present invention does not exceed about 2,500. More preferably, the molecular weight does not exceed about 1,750. Even more preferably the molecular weight does not exceed about 1200. Compounds may bear more than one fluorous tag of the present invention.

In one aspect, the present invention provides a method of increasing the fluorous nature of a compound, including the step of reacting the compound with at least one second compound having the formula:

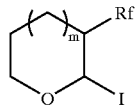

wherein Rf is a fluorous group and m is 0, 1 or 2 (that is, the ring can be a five-, six-, or seven-membered ring). The fluorous group can, for example be a fluorohydrocarbon group (for example, fluorous alkyl groups, including fluorous adamantyl groups), a perfluorocarbon group, a fluorinated ether group or a fluorinated amine group. Perfluoroadamantyl group suitable for use in the present invention can, for example, have the following formulas:

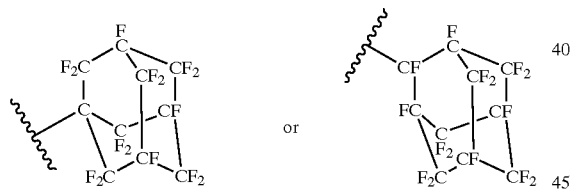

As used herein, the terms "alkyl", "aryl" and other substituent groups refer generally to both unsubstituted and substituted groups unless specified to the contrary. Unless otherwise specified, alkyl groups are hydrocarbon groups and are preferably $C_1$–$C_{15}$ (that is, having 1 to 15 carbon atoms) alkyl groups, and more preferably $C_1$–$C_{10}$ alkyl groups, and can be branched or unbranched, acyclic or cyclic. The term "aryl" refers to phenyl (Ph) or napthyl, substituted or unsubstituted. The term "alkylene" refers to bivalent forms of alkyl.

The groups set forth above, can be substituted with a wide variety of substituents. For example, alkyl groups may preferably be substituted with a group or groups including, but not limited to aryl groups. Aryl groups may preferably be substituted with a group or groups including, but not limited to, alkyl groups or other aryl groups.

In another aspect, the present invention provides a method of increasing the fluorous nature of a compound, including the step of reacting the compound with at least one second compound having the formula:

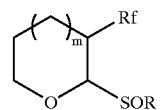

wherein Rf is a fluorous group as defined above, $R^1$ is a an alkyl group or an aryl group and m is 0, 1 or 2.

A method of increasing the fluorous nature of a compound, including the step of reacting the compound with at least one second compound having the formula:

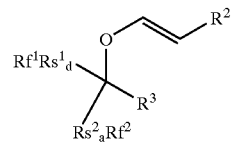

wherein $Rf^1$ and $Rf^2$ are independently, the same or different, fluorous groups, $Rs^1$ is a spacer group, d is 1 or 0 (that is, the spacer group can be present or absent), $Rs^2$ is a spacer group, a is 1 or 0, $R^2$ is a H, an alkyl group or an aryl group, $R^3$ is H or —$Rs^3{}_e Rf^3$, wherein, $Rs^3$ is a spacer group, e is 1 or 0, and $Rf^3$ is a fluorous group. Numerous types of spacer groups or linkages can be used in the present invention. Examples of spacer groups suitable for use herein include, but are not limited to, alkylene groups (preferably, $C_1$–$C_6$ alkylene groups), 1,2-, 1,3-, or 1,4-divalent phenyl groups or alkoxy alkylene groups (for example, —O(CH$_2$)$_x$—). As used herein, the term "alkylene" refers generally to a bivalent form of an alkyl group (for example, —(CH$_2$)$_m$—) Alkylene groups may be substituted or unsubstituted.

The present invention also provides a method of increasing the fluorous nature of a compound, including the step of reacting the compound with at least one second compound having the formula:

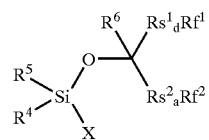

wherein $Rf^1$ and $Rf^2$ are independently, the same or different, fluorous groups, $Rs^1$ is a spacer group, d is 1 or 0 (that is, the spacer group can be present or absent), $Rs^2$ is a spacer group, a is 1 or 0, $R^4$ is an alkyl group or an aryl group, $R^5$ is an alkyl group or an aryl group, $R^6$ is H, an alkyl group, or a fluorinated alkyl group, and X is Cl, Br or I.

In another aspect, the present invention provides a method of increasing the fluorous nature of a compound, including the step of reacting the compound with at least one second compound having the formula:

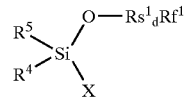

wherein $Rf^1$ is a fluorous group, $Rs^1$ is a spacer group, d is 1 or 0, $R^4$ is an alkyl group or an aryl group, $R^5$ is an alkyl group or an aryl group, and X is Cl, Br or I.

The present invention further provides a compound having the formula:

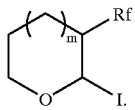

The present invention also provides a compound having the formula:

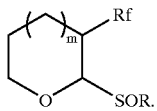

The present invention also provides a compound having the formula:

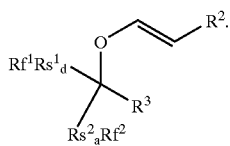

The present invention also provides a compound having the formula:

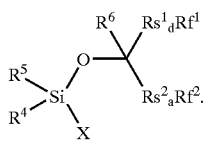

The present invention further provides a compound having the formula:

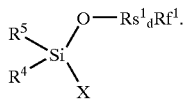

In another aspect, the present invention provides a method of activating an anomeric sulfoxide to react with an alcohol to form a corresponding ether comprising the step of mixing the anomeric sulfoxide with $Cp_2ZrCl_2$, $AgClO_4$, and the alcohol. The anomeric sulfoxide can, for example, have the formula:

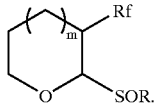

In still another aspect, the present invention provides a method of carrying out a reaction comprising the steps of:
attaching a fluorous tag to a substrate that is bound to a solid support;
cleaving the fluorous-tagged substrate from the solid support while retaining the fluorous tag attached thereto;
reacting the cleaved, fluorous-tagged substrate in a liquid phase reaction to synthesize a fluorous-tagged product; and
separating the fluorous-tagged product from other compounds using a fluorous separation technique.

The method may further include the step of cleaving the fluorous tag from the fluorous tagged product. In one embodiment, the fluorous tag has the formula:

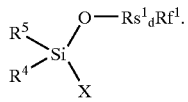

DETAILED DESCRIPTION OF THE INVENTION

Fluorous-Labeled Tetrahydropyranyl ($THP^F$) Ethers

In one aspect the present invention provides a series of fluorous-labeled tetrahydropyranyl ($THP^F$) ethers that are stable to basic and nucleophilic reaction conditions and become readily recyclable after cleavage. A perfluoroalkyl-substituted dihydropyran which can be installed on any hydroxy-bearing substrate via acid catalysis in the same way a standard THP protection is provided as a model.

Figure 1:
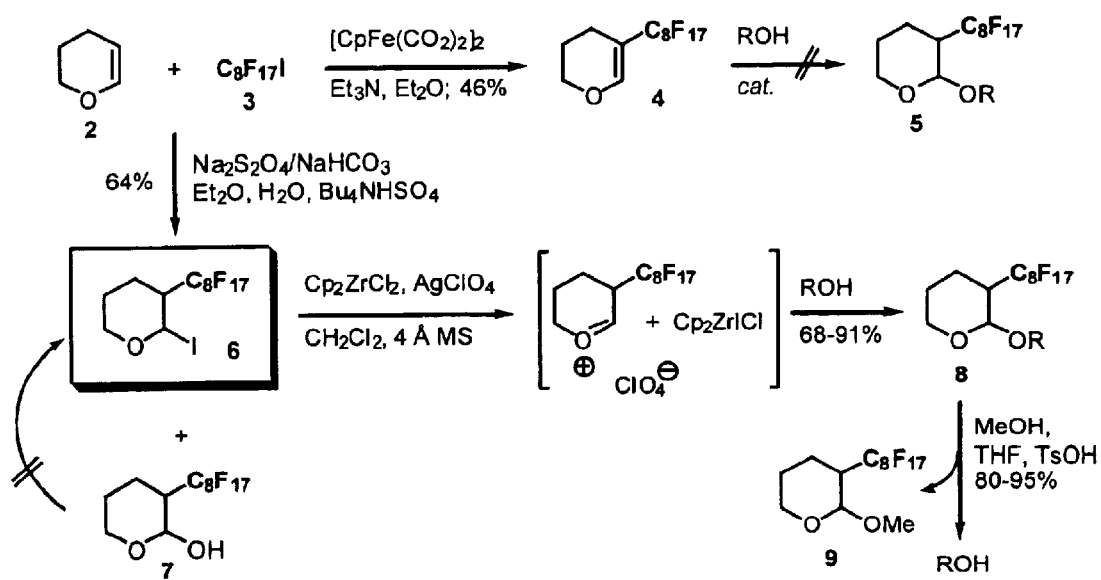
FIG. 1 illustrate synthesis of one embodiment of a fluorous glycosyl iodide tagging compound of the present invention and fluorous-tagged ethers synthesized therefrom.

Initially, dihydropyran 4 was synthesized in one step from perfluorooctyl iodide 3 and dihydropyran 2 in 46% yield as illustrate in FIG. 1. However, treatment of alcohols with an excess of 4 using a variety of acids, solvents, and temperatures failed to give any of the desired acetal 5. The loss of reactivity of the vinyl ether is believed to be a result of the powerful electron withdrawing effect of the perfluoroalkyl chain.

A second route involved glycosylation methodology. Glycosyl fluorides have been effectively activated by a $Cp_2ZrCl_2$—$AgClO_4$ reagent system. Suzuki, K. *Pure Appl. Chem.* 1994, 66, 1557. Flourous glycosyl iodide 6 was accessible in one step from perfluorooctyl iodide 3 with excess dihydropyran and stoichiometric $Na_2S_2O_4$/$NaHCO_3$ under phase transfer conditions in 64% yield. Unfortunately, this reaction was often irreproducible, and was typically plagued by formation of hemiacetal 7. Use of catalytic Raney Nickel in refluxing THF gave 6 more reliability in 32–38% yield. Addition of a slight excess of 6 to a solution of one equivalent of $Cp_2ZrCl_2$, two equivalents of $AgClO_4$, and one equivalent of an alcohol gave good yields of fluorous THP labeled products 8, presumably via an intermediate highly reactive oxonium species. Deprotection via transacetalization with methanol and catalytic para-toluenesulfonic acid proceeded to give the free alcohol in 80–95% yield, as well as the transacetalization product 9. However, attempts to recylcle methyl THP ether 9 to iodopyran 6 have yet to be successful. Application of trimethylsilyl iodide (TMSI) and several of its in situ prepared variants led in all cases to the undesired elimination product 4 as the primary product.

A sulfoxide method, however, has proven to be a mild and effective means for constructing glycosidic linkages. See Yan, L.; Kahne, D. J. Am. Chem. Soc. 1996, 118, 9239, and references cited therein. The synthesis of fluorous tetrahydropyranyl ($THP^F$) ethers of the present invention using this technique, began with the direct synthesis of methyl THP ether 9 from perfluorooctyl iodide 3 and dihydropyran 2. Treatment of a methanolic solution of 3 and 5 mol % $[CpFe(CO)_2]_2$ (cyclopentadienyl iron dicarbonyl dimer) with 1.5 equiv of dihydropyran and 1.1 equiv of $Et_3N$ at room temperature gave 9 in 83% yield. Conversion of 9 to the phenylthioacetal 10 was first accomplished using Nicolaou's method (5 equiv $PhSSiMe_3$ (phenylthiotrimethylsilane), 1.2 equiv $Me_3SiOTf$ (trimethylsilyltrifluoromethanesulfonate)) to give 10 in 60% yield. Nicolaou, K. C.; Seitz, S. P.; Papahatjis, D. P. J. Am. Chem. Soc. 1983, 105, 2430. Alternatively, heating 9 in a 1:1 mixture of PhSH (thiophenol) and toluene at 100° C. with 1 equiv of para-toluenesulfonic acid gave 10 in 61% yield. Oxidation of sulfide 10 with a $Na_2HPO_4$-buffered solution of meta-chloroperoxybenzoic acid in dichloromethane at 0° C. provided fluorous sulfoxide tagging compound 11 as a 1.5:1 mixture of anomers in 72% yield. Subsequent conversion utilized the major, more reactive cis-isomer. Trans-11 could be recycled to a 1:1 mixture of anomers in thiophenol/dioxane (1:1) at 95° C. in the presence of a catalytic amount of $HgSO_4$.

Figure 2:
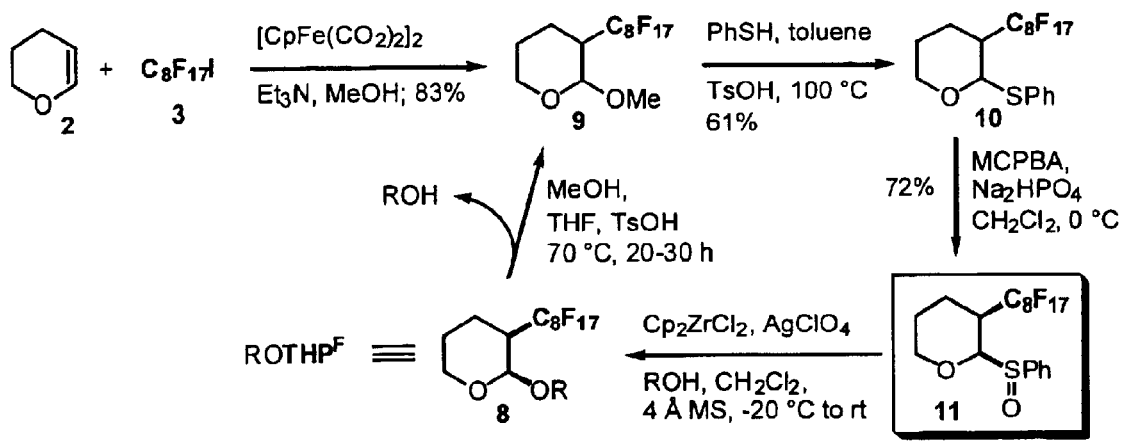
FIG. 2 illustrate synthesis of one embodiment of a fluorous sulfoxide tagging compound of the present invention and fluorous-tagged ethers synthesized therefrom.
Figure 2:
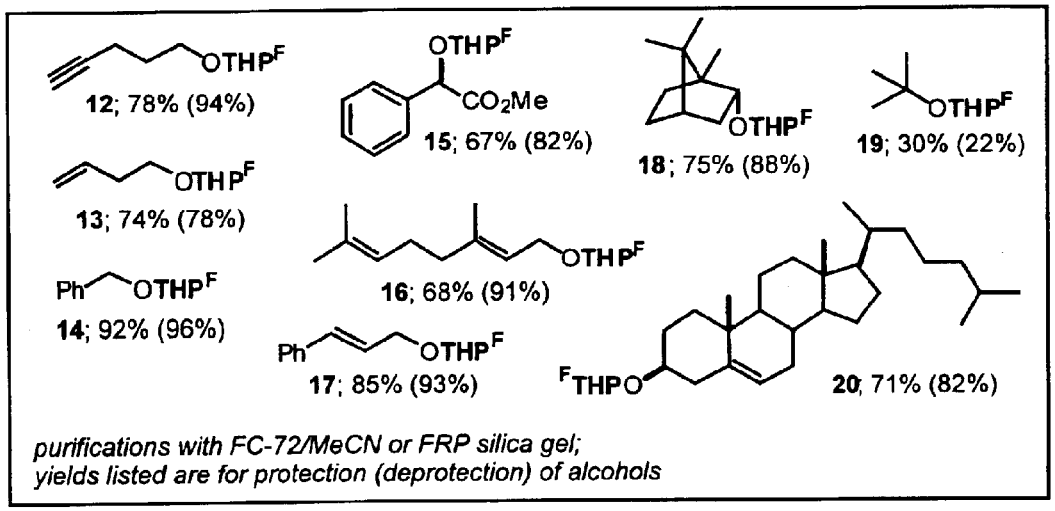

Attempted glycosylation of alcohols with 11 using the standard triflic anhydride/2,6-di-tert-butyl-4-methyl pyridine reagent system gave low yields of 8 contaminated with large amounts of a dihydropyran elimination product 4. In contrast, treatment of a 1:2:1 mixture of $Cp_2ZrCl_2$, $AgClO_4$, and alcohol at −20° C. with 1.5–2.5 equivalents of 11 provided after 8–10 h the desired fluorous THP labeled ethers 12–20 illustrated in FIG. 2 ($ROTHP^F$) in good yields for 1° and 2° alcohols. In addition, deprotection of the $THP^F$-ethers and recycling of the protective group was accomplished by a transacetalization reaction using 25 mol % para-toluenesulfonic acid in MeOH:THF (2:1) at 70° C. for 20–30 h to give good yields of recovered alcohols and 9.

Purification of most $THP^F$-ethers was accomplished simply by dissolving the crude product in MeCN and extracting five times with FC-72. FC-72 is a fluorocarbon solvent commercially available (3M) which includes perfluorohexane ($C_6F_{14}$) isomers (bp 56° C.). Concentration of the fluorous extracts yielded the fluorous product, which contained small amounts of a dihydropyran elimination product 4, as well as trace amounts of unreacted sulfoxide 11. After this extraction, only minor amounts of the fluorous product remained in the MeCN layer. The crude deprotection mixture, treated with the same MeCN/FC-72 extraction procedure, gave the fluorous methyl-THP ether 8 in the FC-72 extracts, while the deprotected alcohol was found in the organic layer. As the organic mass or the polarity of a fluorous THP-labeled substrate becomes larger, however, simple liquid-liquid extraction becomes inefficient. Solid phase extraction by filtration through fluorous reverse-phase (FRP) silica gel was found to be effective for these cases. See Curran, D. P.; Hadida, S.; He, M. J. Org. Chem. 1997, 62, 6714. The rather polar 5 is almost insoluble in FC-72. This is advantageous in terms of separation of excess 11 during extractive purification of $THP^F$-labeled alcohols, but also suggests a sufficiently polar moiety on the substrate to be protected may overpower the fluorous nature of the protected product. Fluorous THP-labeled cholesterol and methyl mandelate could not be fully extracted from MeCN with multiple (15) FC-72 extractions. Loading of the crude product onto a MeCN-wetted FRP-$SiO_2$ column, washing first with MeCN to elute organic components, then with FC-72 to elute the fluorous labeled compounds, conveniently allowed separation of $THP^F$-labeled ethers from organic side products.

The recyclable fluorous THP tag or protecting group enables simple purification of small molecules by liquid-liquid extraction with FC-72/MeCN, and of larger or more polar molecules by solid phase extraction with fluorous reverse phase silica gel.

Fluorous Vinyl Ether Tags

In another aspect, the present invention provides a recyclable fluorous vinyl ether tagging or protecting group that is attached and removed under mildly acidic conditions.

Figure 3:
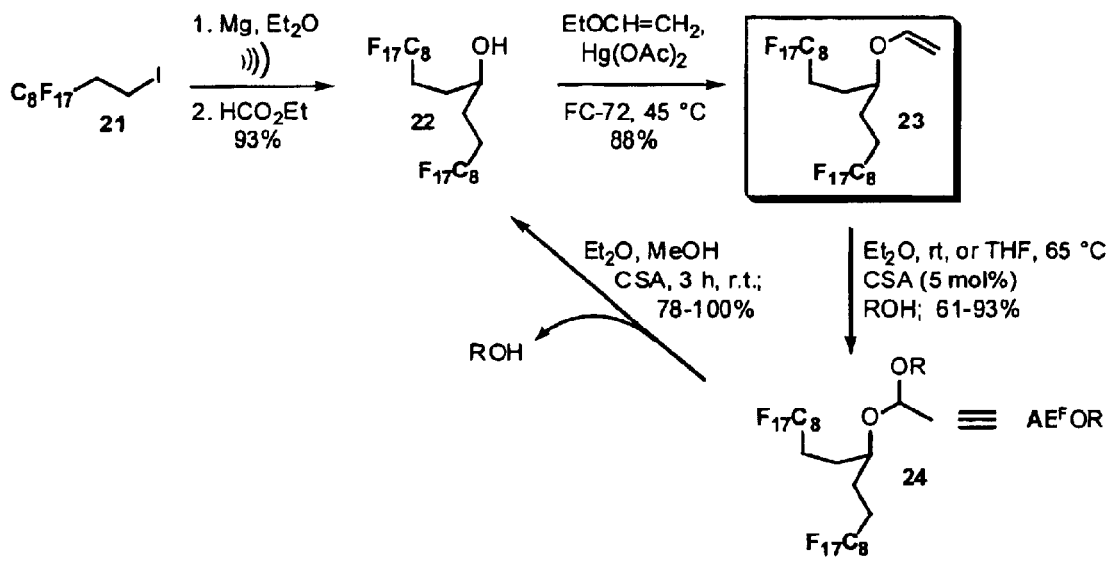
FIG. 3 illustrates synthesis of one embodiment of a fluorous vinyl ether tagging compound of the present invention and fluorous tagged ethers produced therefrom.
Figure 3:
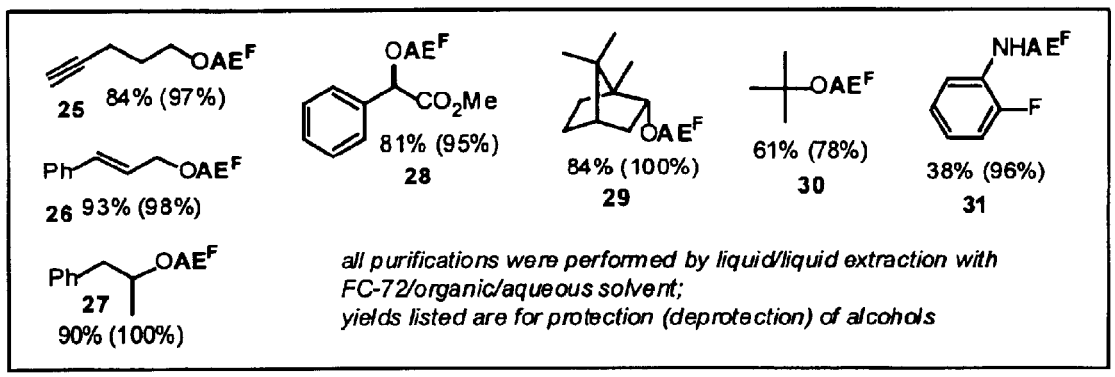

A representative example of the synthesis of a fluorous vinyl ether tagging compound is illustrated in FIG. 3. The synthesis of vinyl ether 23 begins with commercially available iodide 21. Formation of the Grignard reagent from 21 was effectively accomplished with sonication for the reaction initiation. Thus, treatment of an ether suspension of excess magnesium powder with 0.1 equivalents of 21, sonication for 20 minutes, and subsequent addition of an additional 2.4 equivalents of 21 in $Et_2O$ provided the Grignard reagent after a two hour reflux period. Dropwise addition of one equivalent of ethyl formate to the reaction mixture and further refluxing for 5 h gave the crude fluorous alcohol 22 after standard workup. This compound was conveniently purified by washing the crude solid with dichloromethane to give a 93% yield of 22. Vinylation (See Faulkner, D. J.; Petersen, M. R. J. Am. Chem. Soc. 1973, 95, 553) of 22 with 0.5 equivalents of mercuric acetate in a 1:1 mixture of ethyl vinyl ether and FC-72 at 45° C. for 40 h gave fluorous vinyl ether tagging compound 23 in 51% yield, with 42% recovered alcohol 22 (88% yield based on recovered starting material). The extremely apolar 23 could be isolated by filtration of the crude product mixture through a short pad of $SiO_2$ with hexanes, since the RF value of 23 is 0.9 in hexane, while 22 has an $R_F$ close to zero in hexane. The $R_f$ value of a compound is a measure of the relative polarity of the compound in a given solvent system. Thus, a compound with $R_f=1$ is very nonpolar relative to a compound with $R_f=0$, which would be considered very polar. The unreacted 22 can then be resubjected to the vinylation reaction, allowing for a ~70% conversion to 23 after two runs. Accordingly, vinyl ether 23 is readily prepared in multigram quantities.

Protection of alcohols with 23 proceeds under mildly acidic conditions. Treatment of an $Et_2O$ solution of 1 equivalent of a primary alcohol and 3 equivalents of 23 with 5 mol % of camphorsulfonic acid for 3 h at room temperature provided the desired protected alcohols 24 ($ROAE^F$) in 84–93% yields, with the majority of the excess of vinyl ether recoverable. Secondary and even tertiary alcohols are similarly protected in good yields using THF as solvent at 65° C. for 30–45 min. The moderate yield obtained for protection of tert-butyl alcohol compares nonetheless well to the protection of this sterically hindered and volatile substrate with the fluorous THP$^F$ lable discussed above. The alkoxy ethyl (AE$^F$) fluorous label could also be installed on the nitrogen atom of an aniline. All protected and fluorous-tagged substrates were purified from excess 23 by column chromatography on SiO$_2$. Separation was generally very straightforward as a result of the considerable RF-differences between 23 and 24, and the pre-purification of the reaction mixture from organic impurities by extraction with FC-72.

Deprotection of fluorous acetals 25–31 proceeded under mild conditions as well. Treatment of the protected substrates in a 1:1 solution of Et$_2$O and MeOH with 5 mol % of camphorsulfonic acid gave, after 1 h, excellent yields of deprotected substrates as well as a quantitative recovery of fluorous alcohol 22 (see FIG. 3). After completion of the reaction, the products were isolated in pure form by simple 3-phase extraction (reaction mixture/saturated aqueous NaHCO$_3$/FC-72). Alcohol 22 can be resubjected to vinylation to give 23 and thus is efficiently recycled.

The recyclable, highly fluorous acetal protecting group have broad applications in fluorous synthesis as well as in fluorous/solid phase combinations and other parallel synthesis strategies. The precursor vinyl ether 23 can be prepared in large quantities in a straightforward two step reaction sequence. Primary, secondary, and tertiary alcohols can be protected in good to excellent yields. The N-protection of 2-fluoroaniline also demonstrates the feasibility of using 23 with amines. After protection with the AE$^F$-groups of the present invention, a compound is capable of undergoing a series of reactions in which purification of products can, for example, be accomplished by simple liquid-liquid extraction with FC-72 or filtration through fluorous reverse-phase SiO$_2$. Deprotection occurs under mild acidic conditions, and the fluorous label is easily isolated and effectively recycled.

Compared to the THP$^F$-function described above, the AE$^F$-groups of the present invention are more readily cleaved and recycled and have a higher affinity toward the fluorous environment. There is a direct correlation between the number of fluorine atoms in a molecule and its selective solubility in perfluorinated solvents. With the exception of small organic molecules, most compounds protected with the THP$^F$-function were insufficiently fluorous for efficient liquid-liquid extraction and rapid purification required fluorous reverse-phase SiO$_2$ (FRP). In particular in preparative scale synthesis, the broad use of FRP chromatography is currently limited by the high costs of the stationary phase. Because of the higher level of fluorination of the AE$^F$-group, all substrates shown in FIG. 3 could be purified by simple liquid-liquid extraction. The AE$^F$-group tags or labels are, therefore, ideally suited for the protection of large quantities or high molecular weight organic molecules under basic and/or nucleophilic reaction sequences. Application of the AE$^F$-fluorous tagging compounds of the present invention to a combinatorial synthesis of analogs of the antimitotic natural product curacin A is discussed below.

tert-Butyl-phenyl-1H,1H,2H,2H-heptadecafluorodecyloxysilyl (BPFOS) Tags

In still another aspect, the present invention provides fluorous alkoxysilyl tagging groups. In general, tert-Butyl-phenyl-1H,1H,2H,2H-heptadecafluorodecyloxysilyl (BPFOS) ethers resulting from reaction of the fluorous alkoxysilyl tagging groups of the present invention with alcohols were found to be surprisingly acid stable and allow simple protection-purification-deprotection schemes by liquid-liquid extraction with FC-72/CH$_3$CN or by solid phase extraction with fluorous reverse phase silica gel.

Figure 4:
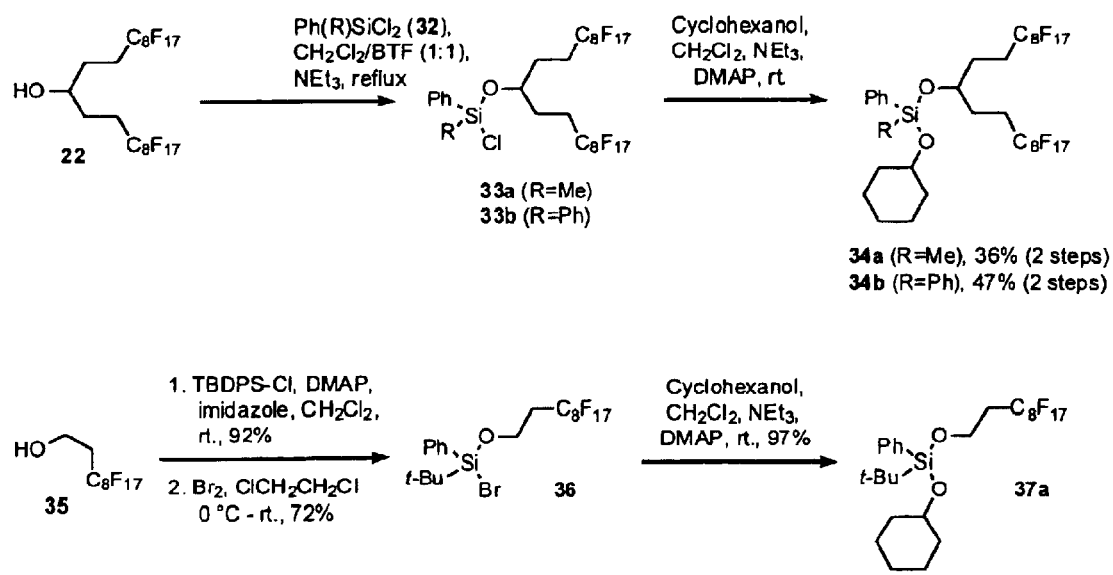
FIG. 4 illustrates synthesis of one embodiment of a fluorous alkoxysilyl tagging compound of the present invention and fluorous tagged ethers produced therefrom.

Given the acid stability of bis-alkoxysilyl ethers, the viability of fluorous alkoxysilyl groups as fluorous tagging/protecting groups for alcohols was explored. A secondary alcohol, cyclohexanol, was chosen as a model compound for tagging. As illustrated in FIG. 4, fluorous alkoxysilyl ethers (34a,b) were readily prepared by reacting stoichiometric amounts of commercially available dichlorosilanes 32 with fluorous alcohol 22 to yield chlorosilanes 33a,b, which were however contaminated with the bis-adduct of the fluorous alcohol. Without purification, 33a,b were used to protect cyclohexanol as illustrated in FIG. 4. The ensuing mixture was purified by solid phase extraction on fluorous reverse phase silica gel with hexane/acetone (50:1). The indicated yields were isolated yields after separation from bis-adducts of the fluorous alcohol. Conversion based on cyclohexanol was quantitative.

Alkoxysilyl ether 37a was derived from bromosilane 36, which can easily be obtained in high yield and purity in a two step sequence starting from tert-butyldiphenylsilylchloride (TBDPS-Cl) and alcohol 35 as illustrated in FIG. 4.

Fluorous alkoxysilyl ethers (34a,b, 37a) were each dissolved in a mixture of CH$_2$Cl$_2$/trifluoroacetic acid (5%), and aliquots of these solutions were quenched with MeOH/pyridine (20:1). The quenched reaction mixtures were analyzed for remaining 34a,b and 37a by LC-MS (Liquid chromatography-mass spectrometry). Reactions and quenching were performed on a HP 7868 solution phase synthesizer. Analysis of quenched samples was done with a HP 1100 series LC/MS. Samples eluted were compared with unreacted control samples. (R$_t$ [min]: 2.6 (34a), 2.9 (34b), 2.3 (37a); Novapak C$_{18}$, 3.9×150 mm, 1.2 mL/min, MeOH as eluent).

The stability of these alkoxysilyl ethers appeared to be determined by the steric bulk around the silicon atom. While 34a was not very stable (t$_{1/2}$~6 min) under the acidic reaction conditions, 34b (t$_{1/2}$~4 h) was moderately stable, and the tert-butyl-phenyl-1H,1H,2H,2H-heptadecafluorodecyloxysilyl ether 37a (t$_{1/2}$>>6 h) was very stable. These results prompted investigation of the chemical behavior of 37a in somewhat greater detail. As a result of the enhanced electrophilicity of the silicon atom in bis-alkoxysilyl ethers, the latter are generally more labile toward nucleophiles and bases than either the TBDPS or the tert-butyldimethylsilyl (TBDMS) groups. Yet, after dissolving 37a in a mixture of THF-d$_8$ and 0.25 M NaOD (3:1), a t$_{1/2}$ of 48 h was determined by $^1$H NMR, suggesting that the tert-butyl-phenyl-1H,1H,2H,2H-hepta-decafluorodecyloxysilyl (BPFOS) tag can be used in mildly basic aqueous media. In contrast, the stability under protic acidic conditions in 5% p-TsOH/MeOH (t$_{1/2}$~40 min) is more limited. Based on these results, it appears that the BPFOS group is closely related in stability to the tert-butylmethoxyphenylsilyl group, which is slightly more acid-labile than the TBDPS function but considerably more acid-stable than a TBDMS-ether.

Figure 5:
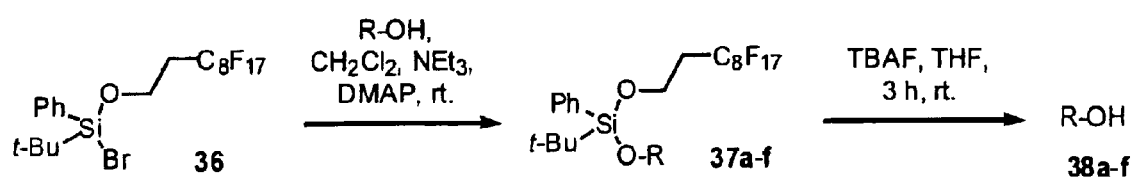
FIG. 5 illustrates the tagging of a number of alcohols with the fluorous alkoxysilyl tag of FIG. 4 and subsequent regeneration of the alcohol and recycling of the fluorous alkoxysilyl tag.

The viability of the tert-butyl-phenyl-1H,1H,2H,2H-heptadecafluorodecyloxysilyl (BPFOS) protecting group for the protection of alcohols in a parallel synthesis experiment performed on a HP 7868 solution phase synthesizer was also studied. Silylbromide 36 was reacted with a panel of alcohols to yield the bis-alkoxysilyl ethers 37a–f as illustrated in FIG. 5. In general, alcohols 38a–f (0.16 mmol) were added to a solution containing the appropriate amount of reagents in 0.7 mL of CH$_2$Cl$_2$. The samples were vortexed and left for 16 h. The solutions were washed with H$_2$O, the organic phase was evaporated and the residue was eluted with hexane through cartridges containing SiO$_2$.

Table 1 summarizes data for the protection of alcohols 38a–f with 36 as set forth in the following equation (and deprotection of silyl ethers with TBAF (tetrabutylammonium fluoride)). [ ] Yields were based on isolated and characterized material ($^1$H NMR, MS) and were slightly lower than reported for the bulk synthesis of 37a as a result of loss of material in the liquid-liquid extraction steps on the synthesizer. Purification in the deprotection step was via FC-72/CH$_3$CN liquid-liquid extraction and filtration through silica gel, and provided material of >90% purity. During the deprotection step, silyl ethers 37a–f were added to a solution of TBAF (0.6 M) in 0.5 mL of THF. After 3 hours, Et$_2$O was added, the solutions were washed with H$_2$O (3 times), the Et$_2$O phase was collected, evaporated and the residue was partitioned between FC-72 and CH$_3$CN. The organic phase was eluted with hexane/AcOEt through a SiO$_2$ cartridge.

TABLE 1

| Entry | R—OH | Yield for BPFOS attachment [%] | Yield for BPFOS cleavage [%] |
|---|---|---|---|
| 1 |  38a | 79 | 77 |
| 2 | 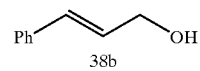 38b | 77 | 88 |
| 3 | 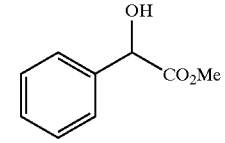 38c | 24 | nd |
| 4 | 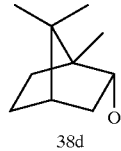 38d | 83 | 94 |
| 5 | 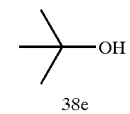 38e | 27 | nd |
| 6 | 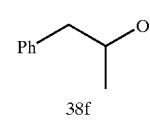 38f | 62 | 100 |

Primary and secondary alcohols gave excellent to fair yields in the protection and deprotection steps while, probably for steric reasons, the tertiary alcohol t-butanol (entry 5) and the sterically demanding methyl mandelate (entry 3) provide less favorable yields.

In summary, new acid stable fluorous silane tag suitable for the protection of primary and secondary alcohols have been developed. The tag is easily attached and removed in an automated parallel synthesis setup and allows for purification of intermediates and products via fluorous liquid-liquid or solid phase extraction.

Exemplary Applications

Figure 6:
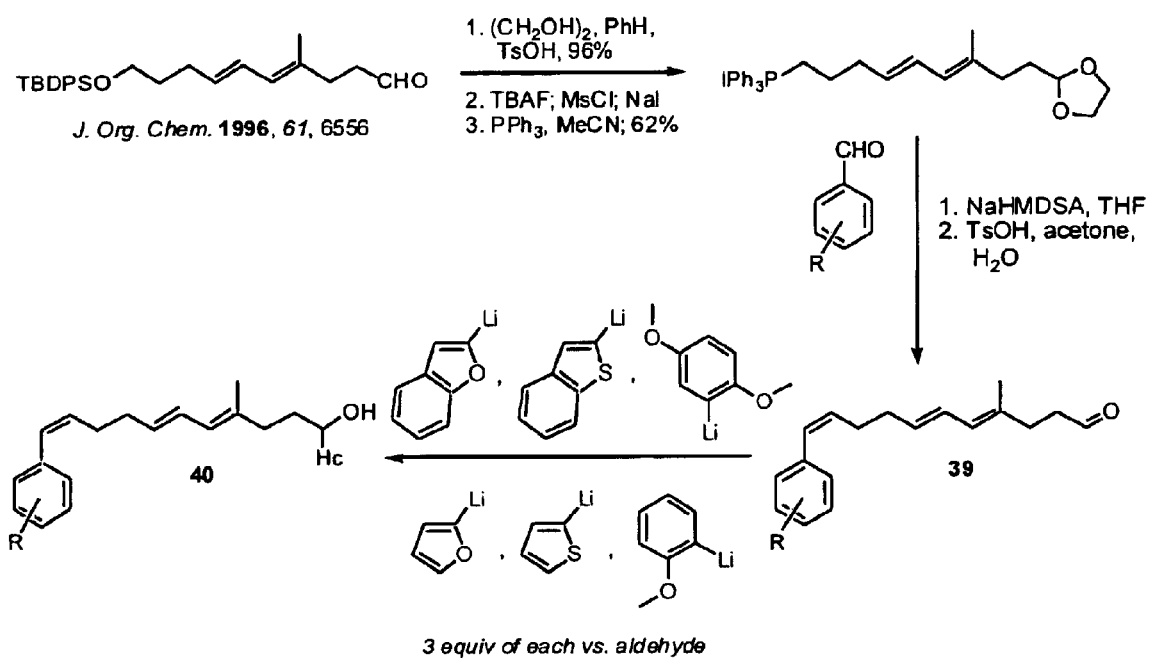
FIGS. 6 and 7 illustrate synthesis of combinatorial mixtures using the fluorous tag of FIG. 3.
Figure 7:
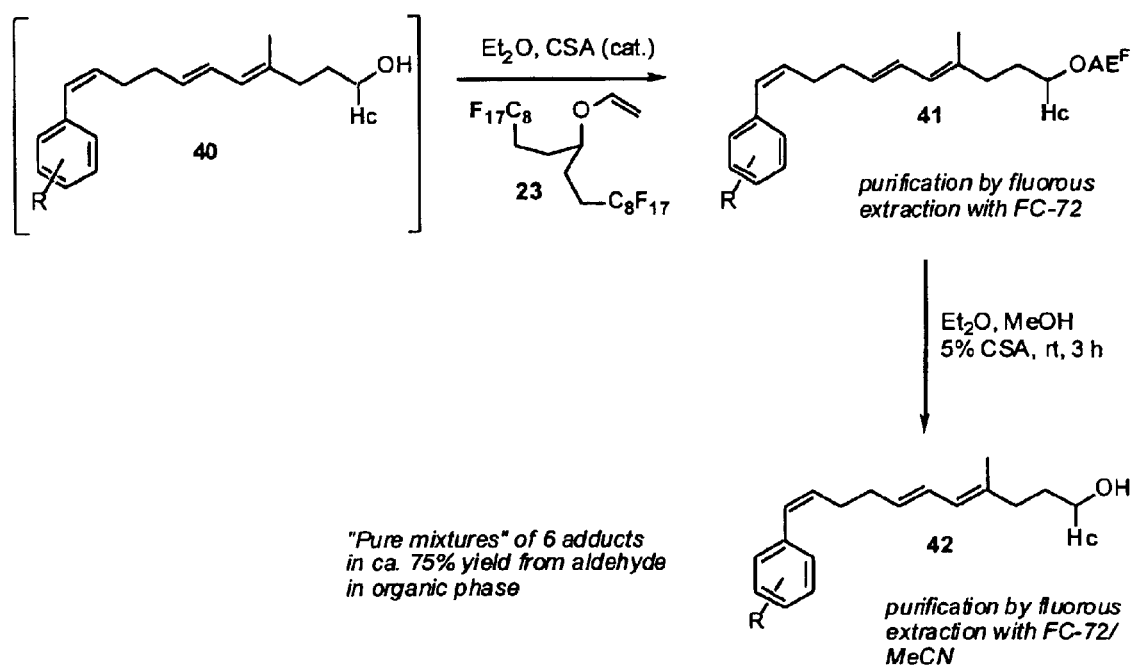
Figure 8:
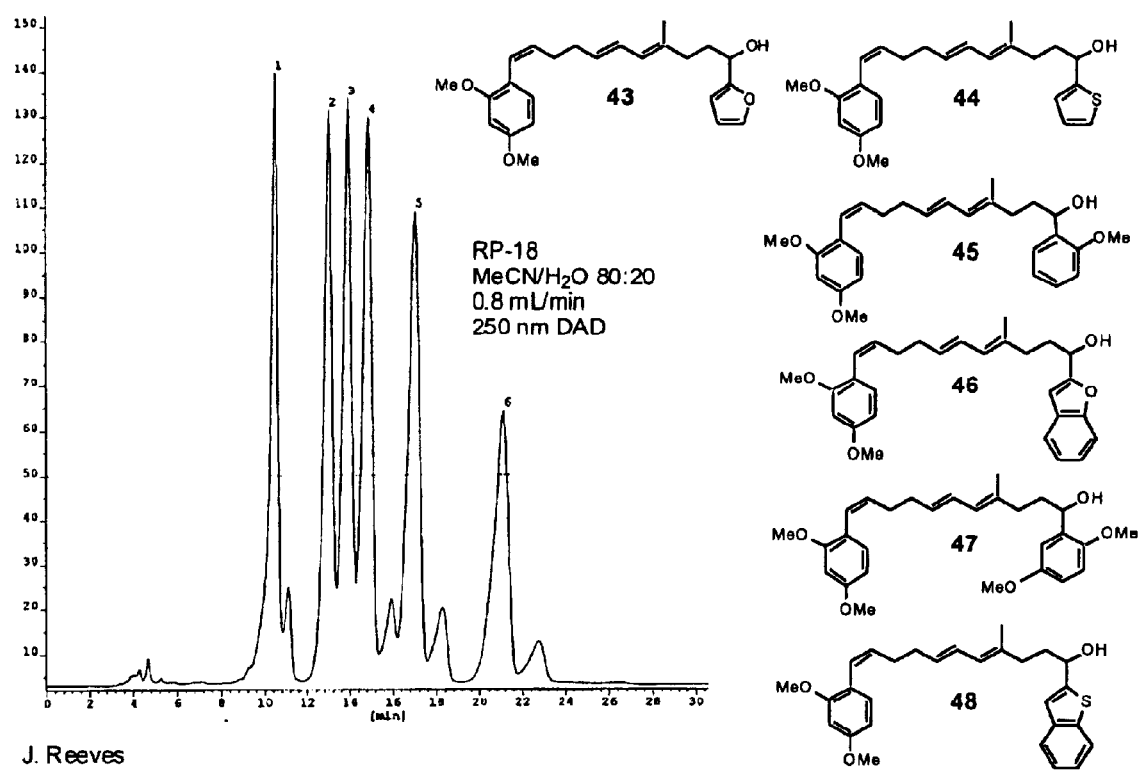
FIG. 8 illustrates characterization of several products of the synthesis of FIGS. 6 and 7 (peaks 1–6 correspond to compounds 43–48, respectively).

Two model applications serve to illustrate the potential use of the newly developed fluorous tags of the present invention. For example, FIG. 6 illustrates the preparation of aldehyde 39 which is subjected to an in situ obtained mixture of six organolithium reagents. The excess of reagents converts the aldehyde rapidly to adduct 40, which is trapped by addition of AE$^F$ vinyl ether tag 23 as illustrated in FIG. 7. Only the desired secondary alcohol products are rendered fluorous with this approach and converted to acetals 41, which are readily purified by fluorous techniques, or, if required, by chromatography. The stability of the AE$^F$ protective group allowed easy manipulation of these products even in an aqueous basic environment, conditions that would lead to immediate decomposition of the earlier silyl ether based tags. After separation from the byproducts and reagents, compounds 41 are de-tagged, and the desired mixture of alcohols 42 is obtained in high yield ready for biological testing. The very high level of combinatorial mixture purification that can be obtained with this approach is demonstrated by the LC-MS trace shown in FIG. 8.

Figure 9:
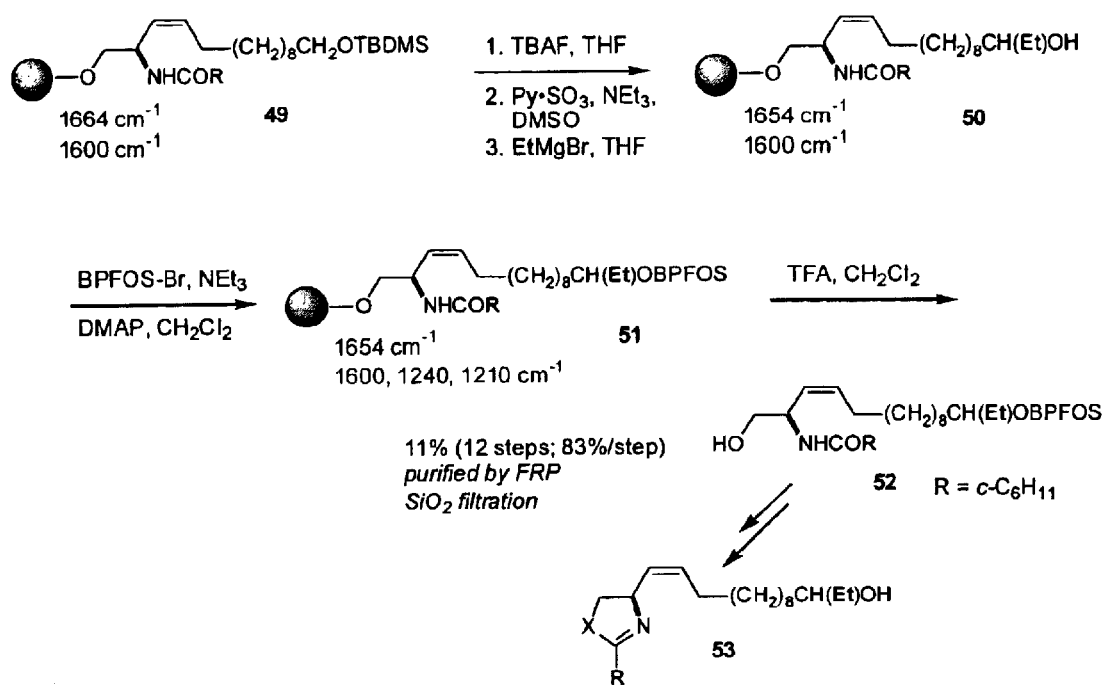
FIG. 9 illustrates an example of conversion from a solid phase synthesis to a liquid phase synthesis using the fluorous tag of FIG. 4.

FIG. 9 illustrates a powerful application for the use of BPFOS tagging compound 36, and demonstrates the first example of a solid phase—fluorous phase switch. Addition of Grignard reagent to the bead-linked aldehyde derived from 49 provides alcohol 50 which is tagged/protected as BPFOS-ether 51 and thus rendered both solid and fluorous. After acidic (TFA) cleavage of the solid support, the BPFOS tagging group allows the extraction of product 52 into the fluorous environment, and subsequent solution phase chemistry can immediately take advantage of fluorous phase purification techniques. No existing fluorous silyl ether tag has the stability necessary to allow this conversion.

Experimental Examples

Compounds 12–20, were obtained in pure form and fully characterized. Cis-11: Mp 66–69° C.; IR (KBr) 3063, 2919, 2853, 1664, 1603, 1445, 1199 cm$^{-1}$; $^1$H NMR (CDCl$_3$)δ 8.00–7.90 (m, 2H), 7.70–7.55 (m, 3H), 4.87 (d, 1H, J=4.3 Hz), 4.50 (dt, 1H, J=11.5, 3.4 Hz), 3.72–3.66 (m, 1H), 3.17–3.00 (m, 1H), 2.64–2.56 (m, 1H), 2.05–1.75 (m, 4H); $^{13}$C NMR (CDCl$_3$)δ 136.5, 134.3, 129.3, 128.9, 125.0–105.0 (m, 8 C), 85.6, 63.3, 32.4 (t, 1 C, J=20.1 Hz), 19.9, 17.5; MS (CI) m/z (rel. intensity) 629 ([M+H]$^+$).

General Procedure for Glycosylation. A mixture of 200 mg of powdered molecular sieves (4 Å), zirconocene dichloride (139 mg, 0.48 mmol), silver perchlorate (200 mg, 0.96 mmol), and 5 mL of CH$_2$Cl$_2$ was stirred at room temperature for 10 min. Benzyl alcohol (49.0 µL, 0.47 mmol) was added to the yellow solution, and the temperature was lowered to −20° C. A solution of cis-11 (446 mg, 0.71 mmol) in 10 mL of CH$_2$Cl$_2$ was added, and the reaction mixture was allowed to warm gradually to room temperature. After 10 h, the solution was filtered through a pad of SiO$_2$. After rinsing with CH$_2$Cl$_2$, the filtrate was concentrated and the residue partitioned between 4 mL of MeCN and 15 mL of FC-72. The MeCN layer was washed with 4 additional 10–15 mL portions of FC-72. $^1$H NMR of the combined fluorous extracts showed the desired product 14 as well as elimination product 4 in a 5.3:1 ratio. $^1$H NMR of the MeCN layer showed primarily excess sulfoxide 11. Chromatography of the FC-72 extract on SiO$_2$ (hexanes/Et$_2$O, 97:3) provided pure 14 (264 mg, 0.43 mmol, 92%) as a colorless solid (7.4:1 ratio of diastereomers): Mp 36–37° C.; IR (KBr) 3037, 2966, 2879, 1501, 1450, 1358, 1209, 1147 cm$^{-1}$; Major diastereomer: $^1$H NMR δ (CDCl$_3$) 7.37–7.29 (m, 5H), 4.99 (d, 1H, J=3.5 Hz), 4.80 (d, 1H, J=11.6 Hz), 4.54 (d, 1H, J=11.7 Hz), 3.97–3.90 (m, 1H), 3.63 (dt, 1H, J=11.3, 5.0 Hz), 2.60–2.40

(m, 1H), 2.20–2.09 (m, 1H), 1.90–1.80 (m, 2H), 1.60–1.50 (m, 1H); $^{13}$C NMR δ (CDCl$_3$) 137.4, 128.5, 128.0, 125.0–105.0 (m, 8 C), 95.2, 69.6, 61.0, 41.3 (t, 1 C, J=19.5 Hz), 21.9, 18.7, 17.4; HRMS (EI) calculated for C$_{20}$H$_{15}$O$_2$F$_{17}$ 610.0801, found 610.0803.

General Procedure for Deprotection of ROTHP$^F$-tagged compounds. A solution of 14 (112 mg, 0.18 mmol) and p-toluenesulfonic acid (9 mg, 0.05 mmol) in 2 mL of MeOH and 2 mL of THF was heated at 70° C. for 24 h. The reaction mixture was diluted with Et$_2$O and washed with a saturated NaHCO$_3$ solution. The organic layer was dried (Na$_2$SO$_4$), concentrated, and partitioned between 2 mL of MeCN and 8 mL of FC-72. The MeCN layer was washed with three 8 mL portions of FC-72. $^1$H NMR analysis of the combined FC-72 extracts showed 9 (82 mg, 0.15 mmol, 84%) with a trace amount of 4. $^1$H NMR analysis of the MeCN layer showed pure benzyl alcohol (19.0 mg, 0.176 mmol, 96%).

Preparation of 22: A suspension of 4.2 g (0.173 mmol) of Mg powder and 2.5 g (4.36 mmol) of iodide 21 in 20 mL of Et$_2$O was sonicated for 20 min. To this black mixture was added dropwise a solution of 22.5 g (39.2 mmol) of iodide 21 in 150 mL of Et$_2$O. The reaction mixture was heated at reflux for 2 h, and the solution was cannulated away from the excess Mg into a new flask. After dropwise addition of 1.40 mL (17.4 mmol) of ethyl formate, the black solution was heated at reflux for 5 h. The reaction mixture was cooled to 0° C., quenched with saturated ammonium chloride solution and extracted with Et$_2$O. The organic extracts were dried (Na$_2$SO$_4$) and concentrated. The crude product was washed with CH$_2$Cl$_2$ and dried in vacuo to give 14.92 g (16.15 mmol, 93%) of 22 as a white solid: Mp 98–101° C.; IR (KBr) 3461, 1204, 1146 cm$^{-1}$; $^1$H NMR (CDCl$_3$)δ 4.20 (d, 1H, J=6.0 Hz), 3.80–3.73 (m, 1H), 2.60–2.15 (m, 4H), 1.95–1.65 (m, 4H); $^{13}$C NMR (TFA)δ 125.0–105.0 (m, 16 C), 79.4, 28.4, 25.9; MS (EI) m/z (rel. intensity) 907 ([M-OH]$^+$, 2), 887 (6), 477 (100).

Preparation of 23: A mixture of 14.92 g (16.15 mmol) of 22, 2.6 g (8.1 mmol) of Hg(OAc)$_2$, 100 mL of ethyl vinyl ether, and 100 mL of FC-72 (commercially available from 3M) was heated at reflux for 40 h. After cooling to room temperature, the reaction mixture was transferred to a separatory funnel, and the layers were separated. The organic layer was extracted with FC-72 (3×), and the combined FC-72 extracts were dried (Na$_2$SO$_4$), and concentrated. The crude product was loaded onto a short (1.5") pad of SiO$_2$ and washed with hexanes until no more 23 was shown to be eluting via TLC. The hexane washings were concentrated to give 7.85 g (8.2 mmol, 51%) of 23 as a white solid, Mp 36–38° C. Flushing the SiO$_2$ pad with EtOAc, followed by concentration of the filtrate gave 6.29 g (6.8 mmol, 42%) of 22. Spectroscopic data for 23: IR (KBr) 3131, 1646, 1617, 1209, 1151 cm$^{-1}$; $^1$H NMR (CDCl$_3$)δ 6.27 (q, 1H, J=6.6 Hz), 4.35 (d, 1H, J=14.2 Hz), 4.10 (d, 1H, J=6.5 Hz), 3.91 (p, 1H, J=5.5 Hz), 2.35–2.00 (m, 4H), 1.95–1.75 (m, 4H); $^{13}$C NMR (CDCl$_3$)δ 150.0, 125.0–105.0 (m, 16 C), 89.8, 76.4, 26.7 (t, J=22.1 Hz), 24.8; MS (EI) m/z (rel. intensity) 950 (M$^+$, 7), 887 (20), 391 (100).

Protection of cinnamyl alcohol: To a solution of 10.5 mg (0.08 mmol) of cinnamyl alcohol and 223 mg (0.24 mmol) of 23 in 3 mL of Et$_2$O was added 1 mg (5 mol %) of 10-camphersulfonic acid (CSA). The solution was stirred at room temperature for 3 h. Saturated NaHCO$_3$ solution was added, and the reaction mixture was extracted with FC-72 (3×). The combined FC-72 extracts were dried (Na$_2$SO$_4$), and concentrated. Column chromatography on SiO$_2$ (hexanes/Et$_2$O, 95:5) gave 101 mg (0.11 mmol, 64%) of 23 and 79 mg (0.073 mmol, 93%) of the desired AE$^F$-protected cinnamyl alcohol as a colorless oil: IR (neat) 3032, 2981, 1491, 1204, 1148, 907 cm$^{-1}$; $^1$H NMR (CDCl$_3$)δ 7.38–7.21 (m, 5H), 6.60 (d, 1H, J=15.9 Hz), 6.25 (dt, 1H, J=5.9, 15.9 Hz), 4.81 (q, 1H, J=5.3 Hz), 4.26–4.13 (m, 2H), 3.80 (p, 1H, J=5.5 Hz), 2.40–2.00 (m, 4H), 1.90–1.75 (m, 4H), 1.37 (d, 3H, J=5.2 Hz); $^{13}$C NMR (CDCl$_3$)δ 136.6, 132.4, 128.7, 127.9, 126.5, 125.4, 125.0–105.0 (m, 16 C), 99.0, 73.4, 65.8, 26.4, 20.4; MS (EI) m/z (rel. intensity) 951 ([M-OCH$_2$CHCHPh]$^+$, 9), 887 (9), 577 (8), 477 (50), 118 (100).

Deprotection of AE$^F$-protected cinnamyl alcohol: A solution of 71 mg (0.065 mmol) of AE$^F$-OCH$_2$CH=CH-Ph and 1 mg (5 mol %) of CSA in 1 mL of MeOH and 1 mL of Et$_2$O was stirred at room temperature for 1 h. The reaction mixture was then transferred to a separatory funnel, and saturated NaHCO$_3$ solution and FC-72 were added. The organic and aqueous layers were washed with FC-72 (3×). The combined FC-72 extracts were dried (Na$_2$SO$_4$), and concentrated to give 60 mg (100%) of 22. The organic layer was dried (Na$_2$SO$_4$), and concentrated to give 8.6 mg (98%) of cinnamyl alcohol.

Preparation of 34b: A solution of dichlorodiphenylsilane (0.7 mmol), alcohol 22 (0.7 mmol) and triethylamine (0.77 mmol) in a mixture of CH$_2$Cl$_2$ (2.5 mL) and benzotrifluoride (BTF, 2.5 mL) was heated at reflux for 1.5 d. Solvents were evaporated and the residue was partitioned between FC-72 and CH$_2$Cl$_2$. The FC-72 phases were combined and evaporated. The residue was dissolved in CH$_2$Cl$_2$ (5 mL). Cyclohexanol (0.47 mmol), triethylamine (0.65 mmol) and dimethylaminopyridine (DMAP, 0.02 mmol) were added and the mixture was stirred at room temperature overnight. 3-Phase extraction (NaHCO$_3$ solution, CH$_2$Cl$_2$, FC-72) yielded after pooling and evaporation of the FC-72 phase a colorless oil. Filtration over fluorous reverse phase silica (hexane/acetone 50:1) gave 0.24 g (47%) of 34b as a colorless oil which solidified upon standing: $^1$H NMR (CDCl$_3$)δ 7.62–7.59 (m, 4H), 7.45–7.35 (m, 6H), 3.98–3.92 (m, 1H), 3.82–3.73 (m, 1H), 2.3–1.9 (m, 4H), 1.9–1.6 (m, 8H), 1.5–1.3 (m, 3H), 1.2–1.0 (m, 1H); $^{13}$C NMR (CDCl$_3$)δ 134.9, 132.8, 130.5, 128.0, 125–105 (m, 16C), 71.8, 70.6, 35.5, 27.4, 27.2 (b), 25.4, 23.9; MS(EI) m/z (rel. intensity) 1204 (M$^+$, 4), 1185 (5), 1126 (85).

Preparation of 37a: A solution of TBDPS-CL (26.5 mmol), alcohol 35 (24.1 mmol), DMAP (1.2 mmol) and imidazole (33.8 mmol) in CH$_2$Cl$_2$ (50 mL) was stirred at room temperature overnight. CH$_2$Cl$_2$ was added and the solution was washed with H$_2$O, 1 M HCl and brine. Drying (Na$_2$SO$_4$) and evaporation of the solvent yielded the TBDPS ether as a colorless oil: 15.5 g (92%) $^1$H NMR (CDCl$_3$)δ 7.69–7.66 (m, 4 H), 7.45–7.38 (m, 6H), 3.96 (t, 2H), 2.45–2.25 (m, 2H), 1.07 (s, 9H); $^{13}$C NMR (CDCl$_3$)δ 135.2, 134.9, 129.9, 127.9, 125–105 (m, 8C), 56.3, 33.9 (b), 26.6, 19.1.

Bromine (26.5 mmol) was added dropwise to a solution of the TBDPS et her (22.1 mmol) in 1,2-dichloroethane (150 mL) at 0° C. Stirring continued at room temperature overnight. Distillation (0.03 mbar/105–110° C.) yielded 11.3 g (72%) of 36 as a colorless oil: $^1$H NMR (CDCl$_3$)δ 7.69–7.65 (m, 2 H), 7.48–7.39 (m, 3H), 4.11–4.06 (m, 2H), 2.47–2.35 (m, 2H), 1.01 (s, 9H); $^{13}$C NMR (CDCl$_3$)δ 135.6, 134.9, 131.1, 128.1, 125–105 (m, 8C), 57.0, 34.0 (b), 25.1, 21.4.

36 (1.1 mmol) was dissolved in CH$_2$Cl$_2$ (5 mL). Cyclohexanol (1 mmol), triethylamine (1.4 mmol) and dimethylaminopyridine (DMAP, 0.05 mmol) were added and the mixture was stirred at room temperature overnight. CH$_2$Cl$_2$ was added and the mixture was washed with NaHCO$_3$ solution. The organic phase was dried (Na$_2$SO$_4$), the solvent was removed and the residue filtered through SiO$_2$ (hexane/

EtOAc 98:2) to give 0.70 g (97%) of 37a as a colorless oil: $^1$H NMR (CDCl$_3$)δ 7.65–7.60 (m, 2H), 7.42–7.35 (m, 3H), 4.11 (t, 2H, J=6.9 Hz), 3.95–3.88 (m, 1H), 2.50–2.35 (m, 2H), 1.84–1.72 (m, 4H), 1.52–1.40 (m, 3H), 1.30–1.21 (m, 3H), 0.94 (s, 9H); $^{13}$C NMR (CDCl$_3$)δ 135.5, 132.3, 129.9, 127.8, 125–105 (m, 8C), 71.1, 55.7, 35.7, 34.1 (b), 26.1, 25.6, 23.7, 18.8; HR-MS(EI) m/z found 723.1597, calcd 723.1587.

Reactions and quenching were performed on a HP 7868 solution phase synthesizer. Analysis of quenched samples was done with a HP 1100 series LC/MS. Samples eluted were compared with unreacted control samples. (R$_t$ [min]: 2.6 (34a), 2.9 (34b), 2.3 (37a); Novapak C$_{18}$, 3.9×150 mm, 1.2 mL/min, MeOH as eluent).

Protection of alcohols 38a–f. Alcohols 38a–f (0.16 mmol) were added to a solution containing the appropriate amount of reagents in 0.7 mL of CH$_2$Cl$_2$. The samples were vortexed and left for 16 h. The solutions were washed with H$_2$O, the organic phase was evaporated and the residue was eluted with hexane through cartridges containing SiO$_2$.

Deprotection of ethers 37a–f. Silyl ethers 37a–f were added to a solution of TBAF (0.6 M) in 0.5 mL of THF. After 3 h, Et$_2$O was added, the solutions were washed with H$_2$O (3 times), the Et$_2$O phase was collected, evaporated and the residue was partitioned between FC-72 and CH$_3$CN. The organic phase was eluted with hexane/AcOEt through a SiO$_2$ cartridge.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A compound having the formula:

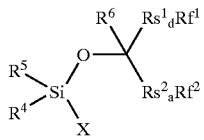

wherein Rf$^1$ and Rf$^2$ are independently, the same or different, a fluorohydrocarbon group, a perfluorocarbon group, a fluorinated ether group or a fluorinated amine group, Rs$^1$ is a spacer group selected from an alkylene group, a divalent phenyl group or an alkoxy alkylene group, d is 1 or 0, Rs$^2$ is a spacer group selected from an alkylene group, a divalent phenyl group or an alkoxy alkylene group, a is 1 or 0, R$^4$ is an alkyl group or an aryl group, R$^5$ is an alkyl group or an aryl group, R$^6$ is H, an alkyl group, or a fluorinated alkyl group, and X is Cl, Br or I.

2. The compound of claim 1 wherein Rf$^1$ and Rf$^2$ are independently perfluoroalkyl groups.

3. The compound of claim 2 wherein the perfluoroalkyl groups have the formula —C$_n$F$_{2n+1}$ wherein n is an integer in the range of 4 to 32.

4. The compound of claim 1 wherein at least one of Rf$^1$ and Rf$^2$ is a perfluoroadamantyl group.

5. The compound of claim 1 wherein R$^5$ is H.

6. A compound having the formula:

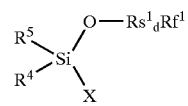

wherein Rf$^1$ is a fluorohydrocarbon group, a perfluorocarbon group, a fluorinated ether group or a fluorinated amine group, Rs$^1$ is a spacer group is a spacer group selected from an alkylene group, a divalent phenyl group or an alkoxy alkylene group, d is 1 or 0, R$^4$ is an alkyl group or an aryl group, R$^5$ is an alkyl group or an aryl group, and X is Cl, Br or I.

7. The compound of claim 6 wherein Rf$^1$ is a perfluoroalkyl group.

8. The compound of claim 7 wherein Rf$^1$ is —C$_n$F$_{2n+1}$ wherein n is an integer in the range of 4 to 32.

9. The compound of claim 6 wherein Rf$^1$ is a perfluoroadamantyl group.

* * * * *